(12) United States Patent
Kim et al.

(10) Patent No.: US 7,494,754 B2
(45) Date of Patent: *Feb. 24, 2009

(54) ELECTROPHOTOGRAPHIC PHOTORECEPTOR CONTAINING ASYMMETRIC NAPHTHALENETETRACARBOXYLIC ACID DIIMIDE DERIVATIVES AND ELECTROPHOTOGRAPHIC IMAGING APPARATUS EMPLOYING THE SAME

(75) Inventors: Beom-jun Kim, Yongin-si (KR); Seung-ju Kim, Suwon-si (KR); Saburo Yokota, Suwon-si (KR); Kyung-yol Yon, Seongnam-si (KR); Moto Makino, Suwon-si (KR); Ji-Young Lee, Suwon-si (KR); Hwan-koo Lee, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 244 days.

This patent is subject to a terminal disclaimer.

(21) Appl. No.: 11/354,145

(22) Filed: Feb. 15, 2006

(65) Prior Publication Data
US 2006/0183044 A1    Aug. 17, 2006

(30) Foreign Application Priority Data
Feb. 16, 2005    (KR) .................... 10-2005-0012899

(51) Int. Cl.
*G03G 5/047*    (2006.01)
(52) U.S. Cl. ............................ 430/78; 430/60; 399/159
(58) Field of Classification Search .................. 430/78, 430/60; 399/159; 546/66
See application file for complete search history.

(56) References Cited

U.S. PATENT DOCUMENTS

2005/0019685 A1 *  1/2005  Kim et al. .................... 430/78
2005/0227156 A1 * 10/2005  Kim et al. .................... 430/78

FOREIGN PATENT DOCUMENTS

| EP | 1340755 | 9/2003 |
| EP | 1340755 A1 * | 9/2003 |
| JP | 5-19510 | 1/1993 |
| JP | 5-27457 | 2/1993 |
| JP | 11-343290 | 12/1999 |
| JP | 11-343291 | 12/1999 |
| JP | 2000-113504 | 4/2000 |

OTHER PUBLICATIONS

Borsenberger, Paul et al. Organic Photoreceptors for Imaging Systems: New York: Marcel-Dekker, Inc. (1993) pp. 289-296.*

* cited by examiner

*Primary Examiner*—Christopher RoDee
(74) *Attorney, Agent, or Firm*—Roylance, Abrams, Berdo & Goodman, L.L.P.

(57) ABSTRACT

An electrophotographic photoreceptor and an electrophotographic imaging apparatus include an asymmetric naphthalenetetracarboxylic acid diimide derivative. The asymmetric naphthalenetetracarboxylic acid diimide derivative has increased solubility in organic solvents and improved compatibility with binder resins, thus providing excellent electron transporting ability. The electrophotographic photoreceptor containing the asymmetric naphthalenetetracarboxylic acid diimide compound according to the present invention can maintain a constant surface potential after being repeatedly used for an extended time. The electrophotographic photoreceptor according to the present invention can provide a high image quality for an extended time.

17 Claims, 3 Drawing Sheets

ELECTROPHOTOGRAPHIC PHOTORECEPTOR CONTAINING ASYMMETRIC NAPHTHALENETETRACARBOXYLIC ACID DIIMIDE DERIVATIVES AND ELECTROPHOTOGRAPHIC IMAGING APPARATUS EMPLOYING THE SAME

CROSS-REFERENCE TO RELATED PATENT APPLICATION

This application claims the benefit of Korean Patent Application No. 10-2005-0012899, filed on Feb. 16, 2005, in the Korean Intellectual Property Office, the disclosure of which is hereby incorporated by reference in its entirety.

BACKGROUND OF THE INVENTION

1. Field of the Invention

The present invention relates to an electrophotographic photoreceptor containing asymmetric naphthalenetetracarboxylic acid diimide derivatives and an electrophotographic imaging apparatus employing the derivatives. More particularly, the invention relates to an electrophotographic photoreceptor containing naphthalenetetracarboxylic acid diimide derivatives having good solubility in an organic solvent and high compatibility with a polymeric binder resin. The invention is also directed to an electrophotographic imaging apparatus employing the electrophotographic photoreceptor.

2. Description of the Related Art

An electrophotographic photoreceptor is used in electrophotography applied to laser printers, photocopiers, CRT printers, facsimile machines, LED printers, liquid crystal printers, and laser electrophotos, and the like. The electrophotographic photoreceptor comprises a photosensitive layer formed on an electrically conductive substrate. The substrate can be in the form of a plate, a disk, a sheet, a belt, or a drum, etc. In electrophotography, an image is formed using an electrophotographic photoreceptor. First, a surface of the photosensitive layer is electrostatically charged uniformly, and then the charged surface is exposed to a pattern of light, thus forming an image. The light exposure selectively dissipates the charge in the exposed regions where the light strikes the surface, thereby forming a pattern of charged and uncharged regions, which is referred to as a latent image. Then, a wet or dry toner is applied in the vicinity of the latent image, and toner droplets or particles deposit in either the charged or uncharged regions to form a toner image on the surface of the photosensitive layer. The resulting toner image can be transferred and fixed to a suitable ultimate or intermediate receiving surface, such as paper. Alternatively, the photosensitive layer can function as the ultimate receptor for receiving the image. The residual toner then is cleaned from the electrophotographic receptor and residual charges are erased. Thus, the electrophotographic photoreceptor can be used repeatedly for long periods.

Electrophotographic photoreceptors are generally categorized into two types. The first is a laminated type having a laminated structure including a charge generating layer comprising a binder resin and a charge generating material (CGM), and a charge transporting layer comprising a binder resin and a hole transporting material (HTM). In general, the laminated type electrophotographic photoreceptor is used in the fabrication of a negative (−) type electrophotographic photoreceptor. The other type is a single layered type in which a binder resin, a CGM, an HTM, and an electron transporting material (ETM) are contained in a single layer. In general, the single layered type photoreceptor is used in the fabrication of a positive (+) type electrophotographic photoreceptor.

The (+) type single layered electrophotographic photoreceptor is advantageous in that it generates a small amount of ozone harmful to humans and since it has a single photosensitive layer, its production costs are low. The most essential material among the materials composing the (+) type single layered electrophotographic photoreceptor is the ETM. Since the hole transporting ability of the HTM is at least a hundred times greater than the electron transporting ability of the commonly used ETM, the performance of the single layered electrophotographic photoreceptor is dependent upon the electron transporting ability of the ETM.

The electron transporting ability of the ETM is greatly affected by its solubility in an organic solvent and compatibility with a polymer binder resin. The conventional ETM includes, for example, a dicyanofluorenone derivative having Formula (i) below, a diphenoquinone derivative having Formula (ii) below, a naphthalenetetracarboxylic acid diimide derivative having Formula (iii) (see U.S. Pat. Nos. 4,992,349 and 4,442,193), and an o-substituted naphthalenetetracarboxylic acid diimide derivative having Formula iv (see U.S. Pat. No. 6,127,076).

(i)

wherein
$R_1$ is a substituted or unsubstituted alkyl group or an aryl group, etc.

(ii)

wherein
$R_1$, $R_2$, $R_3$, and $R_4$ are independently a substituted or unsubstituted alkyl group, a cycloalkyl group, an aryl group, or an alkoxy group, (iii)

wherein
$R_1$ and $R_2$ are independently a substituted or unsubstituted aryl group, a sulfonyl group, a sulfone group, $R_3$, $R_4$, $R_5$, and $R_6$ are independently a hydrogen atom, a $C_{1-4}$ alkyl group, a $C_{1-4}$ alkoxy group, or a halogen atom, and n is 0-3, (iv)

wherein

R is a hydrogen atom, an alkyl group, an alkoxyl group, or a halogen atom, $R_1$ and $R_2$ are different from each other and each is a substituted or unsubstituted alkyl group, an alkoxyl group, or an aryl group, $R_3$ is a hydrogen atom, a substituted or unsubstituted alkyl group, an alkoxyl group, or an aryl group.

The dicyanofluorenone derivative of Formula (i) and the diphenoquinone derivative of Formula (ii) have low solubility in an organic solvent and low inherent electron transporting ability. Thus, electrophotographic photoreceptors manufactured using the derivative (i) or (ii) as the ETM have disadvantages such as a remarkably reduced charge potential and an increased exposure potential after repeated charging exposures.

The naphthalenetetracarboxylic acid diimide derivatives of Formulae (iii) and (iv) are known to have high electron transporting ability. However, these derivatives of Formulae (iii) and (iv) have low solubility in an organic solvent and low compatibility with a polymer binder resin. Electrophotographic photoreceptors manufactured using these derivatives have surfaces of the photosensitive layers that may crystallize (precipitation of ETM), thus adversely affecting the electrostatic properties of the photoreceptors.

Thus, electrophotographic photoreceptors, especially single layered type electrophotographic photoreceptors, manufactured using the conventional ETMs have a remarkably reduced charge potential and an increased exposure potential after repeated use. In general, surface charges of electrophotographic photoreceptors must be maintained at a predetermined potential. Due to the decrease in the charge potential and the increases in the exposure potential, image qualities may be deteriorated.

SUMMARY OF THE INVENTION

The present invention is directed to an electrophotographic photoreceptor including a new naphthalenetetracarboxylic acid diimide derivative having an effective solubility in organic solvents and an effective compatibility with polymer binder resins, and having effective electron transporting ability.

The present invention also provides an electrophotographic imaging apparatus and an electrophotographic cartridge employing the electrophotographic photoreceptor.

The present invention also provides new naphthalenetetracarboxylic acid diimide derivatives.

According to an aspect of the present invention, an electrophotographic photoreceptor includes an electrically conductive substrate, a photosensitive layer formed on the electrically conductive substrate. The photosensitive layer comprises an asymmetric naphthalenetetracarboxylic acid diimide derivative represented by Formula (1):

(1)

wherein $R_1$ and $R_2$ are independently selected from the group consisting of a hydrogen atom, a substituted or unsubstituted $C_1$-$C_{20}$ alkyl group, a substituted or unsubstituted $C_1$-$C_{20}$ alkoxy group, and a halogen atom; $R_3$ and $R_4$ are independently a substituted or unsubstituted $C_1$-$C_{20}$ alkyl group; and Ar is a substituted or unsubstituted $C_6$-$C_{30}$ aryl group.

According to another aspect of the present invention, an electrophotographic imaging apparatus includes an electrophotographic photoreceptor, wherein the electrophotographic photoreceptor includes an electrically conductive substrate, and a photosensitive layer formed on the electrically conductive substrate. The photosensitive layer comprises an asymmetric naphthalenetetracarboxylic acid diimide derivative represented by Formula (1).

According to still another aspect of the present invention, an electrophotographic imaging apparatus includes an electrophotographic photoreceptor unit including an electrically conductive substrate, and a photosensitive layer formed on the electrically conductive substrate. The photosensitive layer comprises an asymmetric naphthalenetetracarboxylic acid diimide derivative represented by Formula (1), a charging device that charges the photoreceptor unit, an imagewise light irradiating device that irradiates the charged photoreceptor unit with imagewise light to form an electrostatic latent image on the photoreceptor unit, a developing unit that develops the electrostatic latent image with a toner to form a toner image on the photoreceptor unit, and a transfer unit that transfers the toner image onto a receiving material.

According to yet another aspect of the present invention, there is provided an electrophotographic cartridge including an electrophotographic photoreceptor comprising an electrically conductive substrate, and a photosensitive layer formed on the electrically conductive substrate, wherein the photosensitive layer comprises an asymmetric naphthalenetetracarboxylic acid diimide derivative represented by Formula (1), and at least one selected from the group consisting of a charging device that charges the electrophotographic photoreceptor, a developing device that develops an electrostatic latent image formed on the electrophotographic photoreceptor, and a cleaning device that cleans a surface of the electrophotographic photoreceptor, the electrophotographic cartridge being attachable to or detachable from the imaging apparatus.

In the electrophotographic imaging apparatus, an intermediate layer may further be provided between the electrically conductive substrate and the photosensitive layer.

According to a further aspect of the present invention, there is provided an asymmetric naphthalenetetracarboxylic acid diimide derivative represented by Formula (1).

These and other aspects of the invention will become apparent from the following detailed description of the invention which, taken in conjunction with the annexed drawings, disclose various embodiments of the invention.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

An electrophotographic photoreceptor according to the present invention and an electrophotographic imaging apparatus employing the same will now be described in detail.

The naphthalenetetracarboxylic acid diimide derivative having Formula 1 according to the present invention has an asymmetric structure, and has improved solubility in organic solvents and an excellent compatibility with polymer binder resins. Accordingly, the asymmetric diimide derivative according to the present invention is an electron transporting material (ETM) that exhibits noticeably improved electron transporting ability and charge stability after a long period of use. Thus, an electrophotographic photoreceptor having effective electrostatic property and durability can be achieved using the ETM represented by Formula 1:

[Formula 1]

wherein $R_1$ and $R_2$ are independently selected from the group consisting of a hydrogen atom, a substituted or unsubstituted $C_1$-$C_{20}$ alkyl group, a substituted or unsubstituted $C_1$-$C_{20}$ alkoxy group, and a halogen atom; $R_3$ and $R_4$ are independently a substituted or unsubstituted $C_1$-$C_{20}$ alkyl group; and Ar is a substituted or unsubstituted $C_6$-$C_{30}$ aryl group.

The halogen atom is preferably fluorine, chlorine, bromine or iodine.

The alkyl group of $R_1$, $R_2$, $R_3$ and $R_4$ is a linear or branched $C_1$-$C_{20}$ alkyl group, preferably a linear or branched $C_1$-$C_{12}$ alkyl group. Examples of the alkyl group include methyl, ethyl, n-propyl, isopropyl, n-butyl, isobutyl, sec-butyl, tert-butyl, pentyl, hexyl, 1,2-dimethyl-propyl, and 2-ethylhexyl. The alkyl group may be substituted with a halogen atom, an alkyl group, an aryl group, an alkoxy group, a nitro group, a hydroxy group, or a sulfonic acid group.

The alkoxy group of $R_1$ and $R_2$ is a linear or branched $C_1$-$C_{20}$ alkoxy group, and preferably a linear or branched $C_1$-$C_{12}$ alkoxy group. Examples of the alkoxy group include methoxy, ethoxy, propoxy, and the like. The alkoxy group may be substituted with a halogen atom, an alkyl group, an aryl group, an alkoxy group, a nitro group, a hydroxyl group, or a sulfonic acid group.

The aryl group is a $C_6$-$C_{30}$ aromatic ring. Examples of the aryl group include phenyl, tolyl, xylyl, biphenyl, o-terphenyl, naphtyl, anthracenyl, phenanthrenyl, and the like. The aryl group may be substituted with an alkyl group, an alkoxy group, a nitro group, a hydroxyl group, a sulfonic acid group or a halogen atom.

Specific examples of the asymmetric naphthalenetetracarboxylic acid diimide derivatives having Formula (1) include the following compounds:

(1)

(2)

(3)

(4)

(5)

-continued (6)

(13)

(14)

(15)

(16)

(7)

(8)

(9)

(10)

(11)

(12)

As evident from structures of Compounds (1) through (16), the naphthalenetetracarboxylic acid diimide derivative according to the present invention has an asymmetric structure in which a branched alkyl group substituted with an aryl group (Ar) at an α-position is bonded to one nitrogen atom of an imide bond of the naphthalenetetracarboxylic acid diimide derivative while a linear or branched alkyl group is bonded to the other nitrogen atom of the other imide bond.

The asymmetric structure of the diimide derivative of the present invention provides improved solubility in organic solvents and excellent compatibility with polymer binder resins. Accordingly, the asymmetric diimide derivative according to the present invention exhibits noticeably improved electron transporting ability and charge stability.

Next, a method of preparing the asymmetric naphthalenetetracarboxylic acid diimide derivative according to the present invention will be described.

The naphthalenetetracarboxylic acid diimide derivative according to the present invention is prepared by reacting a naphthalenetetracarboxylic acid dianhydride having Formula (2) with an amine compound having Formula (3) and an amine compound having Formula (4):

wherein $R_1$, $R_2$, $R_3$, and $R_4$ are defined as above.

In the reaction, a polar organic solvent, for example, dimethylformamide (DMF), dimethylacetamide (DMAc), hexamethylphosphoamide (HMPA), or N-methy-2-pyrrolidone (NMP), may be used. The reaction temperature may be set in the range of from 20° C. lower than the boiling point of the solvent to the boiling point of the solvent, and preferably, in the range of from 10° C. lower than the boiling point of the solvent to the boiling point of the solvent.

Generally, the reaction may be carried out in the following manner. First, the naphthalenetetracarboxylic acid dianhydride compound represented by formula (2) is dissolved in a polar organic solvent such as DMF, DMAc, HMPA, or NMP, and then the compounds having formulas (3) and (4) are added dropwise to the resulting solution. Then, the mixture is refluxed for 3 to 24 hours, preferably 3 to 10 hours, to obtain the naphthalenetetracarboxylic diimide derivative represented by Formula (1). In the reaction, the naphthalenetetracarboxylic acid dianhydride of Formula (2), the amine compound of Formula (3), and the amine compound of Formula (4) may be used in a molar ratio of 1:1:1 to 1:2:2. In the reaction, when the amine compound having Formula (3) or the amine compound having Formula (4) are bonded to both nitrogen atoms in imide bonds of the compound having Formula (2), a symmetric naphthalenetetracarboxylic acid diimide derivative is obtained. The symmetric naphthalenetetracarboxylic acid diimide derivative has low solubility in organic solvents than the asymmetric naphthalenetetracarboxylic acid diimide derivative according to the present invention. Therefore, the asymmetric naphthalenetetracarboxylic acid diimide derivative according to the present invention can be separated using the difference in the solubility in organic solvents.

An electrophotographic imaging apparatus and an electrophotographic cartridge employing the electrophotographic photoreceptor according to the present invention comprising the asymmetric naphthalenetetracarboxylic acid diimide derivative having Formula 1 will now be described.

Figure 1:
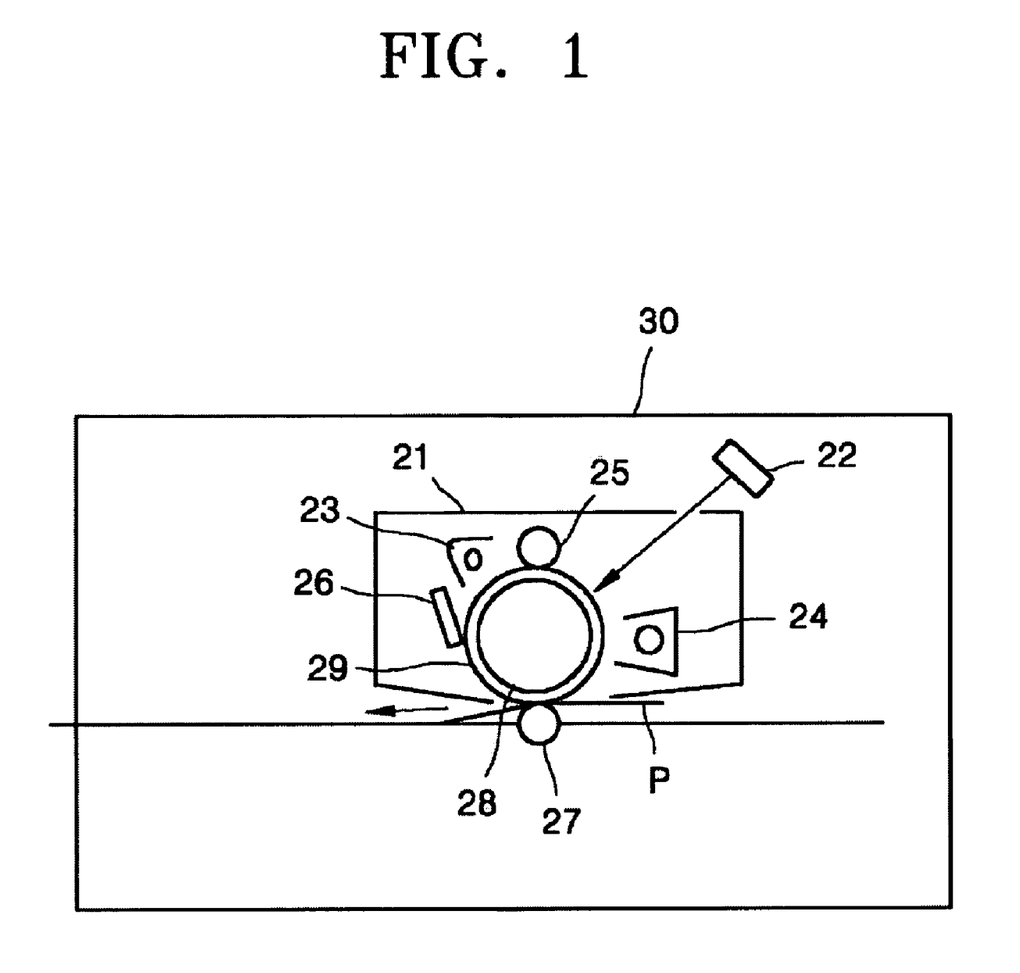
FIG. 1 is a schematic representation of an imaging apparatus showing an electrophotographic drum and an electrophotographic cartridge in accordance with an embodiment of the present invention.

FIG. 1 schematically illustrates an image forming apparatus 30 including an electrophotographic photoreceptor drum 28, 29 and an electrophotographic cartridge 21 according to an embodiment of the present invention. The electrophotographic cartridge 21 typically includes an electrophotographic photoreceptor 29, one or more charging devices 25 for charging the electrophotographic photoreceptor 29, a developing device 24 for developing an electrostatic latent image formed on the electrophotographic photoreceptor 29, and a cleaning device 26 for cleaning a surface of the electrophotographic photoreceptor 29. The electrophotographic cartridge 21 can be attached to and detached from the image forming apparatus 30.

The electrophotographic photoreceptor drum 28, 29 of the image forming apparatus 30 can generally be attached to and detached from the image forming apparatus 30 and includes the drum 28 on which the electrophotographic photoreceptor 29 is placed.

Generally, the image forming apparatus 30 includes a photosensitive unit (for example, the drum 28 and the electrophotographic photoreceptor 29) and the charging device 25 for charging the photoreceptor unit. The apparatus 30 also includes an image-forming light device 22 for irradiating light onto the charged photoreceptor unit to form an electrostatic latent image on the photoreceptor unit. The developing unit 24 for developing the electrostatic latent image with a toner is provided to form a toner image on the photoreceptor unit. A transfer device 27 is provided for transferring the toner image onto a receiving material, such as paper P. The photoreceptor unit includes the electrophotographic photoreceptor 29, which will be described below. The charging device 25 may be supplied with a voltage as a charging unit and may charge the electrophotographic photoreceptor 29. The image forming apparatus 30 may also include a pre-exposure unit 23 to erase residual charge on the surface of the electrophotographic photoreceptor 29 to prepare for a next cycle.

The electrophotographic photoreceptor including the asymmetric naphthalenetetracarboxylic acid diimide derivative having Formula (1) according to an embodiment of the present invention may be incorporated into electrophotographic imaging apparatuses such as laser printers, photocopiers, or facsimiles.

The electrophotographic photoreceptor according to the present invention including the asymmetric naphthalenetetracarboxylic acid diimide derivative represented by Formula (1) employed in the electrophotographic imaging apparatus shown in FIG. 1 will now be described.

The electrophotographic photoreceptor comprises a photosensitive layer formed on an electrically conductive substrate. The electrically conductive substrate may be composed of metal, an electrically conductive polymer, or other material and is produced in the form of a plate, a disk, a sheet, a belt, or a drum. Examples of the metal include aluminum and stainless steel. Examples of the electrically conductive polymer include polyester resin, polycarbonate resin, polyamide resin, polyimide resin, mixtures thereof, and copolymers thereof in which an electrically conductive material, such as electrically conductive carbon, tin oxide, indium oxide, is dispersed.

The photosensitive layer may be a laminated type where a charge generating layer and a charge transporting layer are separately formed, or a single layered type where a layer acts as both a charge generating layer and a charge transporting layer.

The naphthalenetetracarboxylic acid diimide derivative of Formula (1) according to the present invention acts as a charge transporting material, and preferably, as an ETM. In the laminated type photosensitive layer, the naphthalenetetracarboxylic acid diimide derivative of Formula (1) is contained in the charge transporting layer, and in the single layered type photosensitive layer, it is naturally contained in a single layer together with a charge generating material (CGM).

Examples of the CGM used in the photosensitive layer include organic materials such as phthalocyanine pigments, azo pigments, quinone pigments, perylene pigments, indigo pigments, bisbenzoimidazole pigments, quinacridone pigments, azulenium dyes, squarylium dyes, pyrylium dyes, triarylmethane dyes, and cyanine dyes, and inorganic materials such as amorphous silicon, amorphous selenium, trigonal selenium, tellurium, selenium-tellurium alloy, cadmium sulfide, antimony sulfide, and zinc sulfide. The CGM is not limited to the materials listed herein, and may be used alone or in a combination of two or more.

In case of the laminated type photoreceptor, the CGM is dispersed in a solvent with a binder resin and then the dispersion is coated on the electrically conductive substrate by a dip coating, a ring coating, a roll coating, or a spray coating method to form the charge generating layer. The thickness of the charge generating layer is generally about 0.1-1 µm. When the thickness is less than 0.1 µm, the sensitivity is insufficient, and when the thickness is greater than 1 µm, the charging ability and the sensitivity are lowered.

A charge transport layer containing the naphthalenetetracarboxylic acid diimide derivative of Formula (1) is formed on the charge generating layer of the laminated type photosensitive layer, but the charge generating layer may be formed on the charge transport layer in reverse order. When forming the charge transport layer, the naphthalenetetracarboxylic acid diimide derivative of Formula (1) and the binder resin are dissolved in a solvent and the resulting solution is coated on the charge generating layer. Examples of the coating method include a dip coating, a ring coating, a roll coating, and a spray coating method, similar to the methods used to form the charge generating layer. The thickness of the charge transport layer is generally about 5-50 µm. When the thickness is less than 5 µm, the charging ability becomes poor, and when the thickness is greater than 50 µm, the response rate is reduced and the image quality is deteriorated.

When preparing the single layered photoreceptor, the CGM is dispersed in a solvent together with the binder resin and the asymmetric naphthalenetetracarboxylic acid diimide derivative of Formula (1) as the ETM and the resulting dispersion is coated on the electrically conductive substrate to obtain the photosensitive layer. The thickness of the photosensitive layer is generally about 5-50 µm. When the thickness of the single layered photosensitive layer is less than 5 µm, the charging capability and sensitivity are lowered. When the thickness of the single layered photosensitive layer is greater than 50 µm, a residual potential may increase or response speed may decrease. The asymmetric naphthalenetetracarboxylic acid diimide derivative of Formula (1) may be used together with other ETM and/or HTM. In the single layered photoreceptor, it is preferable to use the naphthalenetetracarboxylic acid diimide derivative of Formula (1) together with the HTM.

Examples of the HTM that may be used with the naphthalenetetracarboxylic acid diimide derivative of Formula (1) in the photosensitive layer include nitrogen containing cyclic compounds or condensed polycyclic compounds such as pyrene compounds, carbazole compounds, hydrazone compounds, oxazole compounds, oxadiazole compounds, pyrazoline compounds, arylamine compounds, arylmethane compounds, benzidine compounds, thiazole compounds or styryl compounds. Also, high molecular weight compounds having functional groups of the above compounds on a backbone or side chain may be used.

Examples of other ETM that may be used with the naphthalenetetracarboxylic acid diimide derivative of Formula (1) in the photosensitive layer include, but are not limited to, electron attracting low-molecular weight compounds such as benzoquinone compounds, cyanoethylene compounds, cyanoquinodimethane compounds, fluorenone compounds, xanthone compounds, phenanthraquinone compounds, anhydrous phthalic acid compounds, thiopyrane compounds, or diphenoquinone compounds. Electron transporting polymer compounds or pigments having n-type semiconductor characteristic may also be used.

The ETM or the HTM that may be used with the naphthalenetetracarboxylic acid diimide derivative of Formula (1) in the electrophotographic photoreceptor are not limited to the materials listed herein, and the foregoing materials may be used alone or in combination of two or more.

Examples of solvents used in preparing a coating composition for forming the photosensitive layer include organic solvents such as alcohols, ketones, amides, ethers, esters, sulfones, aromatics, halogenated aliphatic hydrocarbons, and the like. The coating method of the coating composition may be a dip coating method, but a ring coating, a roll coating, a spray coating method, or the like may be also used.

Examples of the binder resin used in the formation of the photosensitive layer include, but are not limited to, polycarbonate, polyester, methacryl resin, acrylic resin, polyvinyl chloride, polyvinylidene chloride, polystyrene, polyvinyl acetate, silicon resin, silicon-alkyd resin, styrene-alkyd resin, poly-N-vinylcarbazole, phenoxy resin, epoxy resin, polyvinyl butyral, polyvinyl acetal, polyvinyl formal, polysulfone, polyvinyl alcohol, ethyl cellulose, phenolic resin, polyamide, carboxy-methyl cellulose and polyurethane. These polymers may be used alone or in a combination of two or more.

The amount of the CTM including the ETM and the HTM in the photoconductive layer may be in the range of 10-60% by weight based on the total weight of the photosensitive layer. If the amount is less than 10% by weight, the sensitivity is insufficient due to low charge transporting ability, thereby resulting in an increased residual potential. If the amount is more than 60% by weight, the amount of the resin in the photosensitive layer is reduced, thereby reducing mechanical strength.

In an embodiment of the present invention, an electroconductive layer may further be formed between the substrate and the photosensitive layer. The electroconductive layer is obtained by dispersing an electroconductive powder such as carbon black, graphite, metal powder or metal oxide powder in a solvent and then applying the resulting dispersion on the substrate and drying it. The thickness of the electroconductive layer may be about 5-50 µm.

In addition, an intermediate layer may be interposed between the substrate and the photosensitive layer or between the electroconductive layer and the photosensitive layer to enhance adhesion or to prevent charges from being injected from the substrate. Examples of the intermediate layer include, but are not limited to, an aluminum anodized layer; a resin-dispersed layer in which metal oxide powder such as titanium oxide or tin oxide is dispersed; and a resin layer such as polyvinyl alcohol, casein, ethylcellulose, gelatin, phenol resin, or polyamide. The thickness of the intermediate layer may be about 0.05-5 µm.

Also, each of the photosensitive layer, the electroconductive layer, and the intermediate layer may further comprise at least one additive selected from a plasticizer, a leveling agent, a dispersion stabilizing agent, an antioxidant, and an optical stabilizer, in addition to the binder resin.

Examples of the antioxidant include phenol compounds, sulfur compounds, phosphorus compounds, or amine compounds. Examples of the optical stabilizer include benzotriazole compounds, benzophenone compounds, or hindered amine compounds.

The electrophotographic photoreceptor according to an embodiment of the present invention may further comprise a surface protecting layer, if necessary.

Hereinafter, the present invention will be described in more detail with reference to the following examples. However, these examples are given for the purpose of illustration and are not intended to limit the scope of the invention.

EXAMPLES

Preparation Example 1

Preparation of Compound (4)

The following is a description of the preparation of asymmetric naphthalenetetracarboxylic acid diimide Compound (4).

(4)

Figure 2:
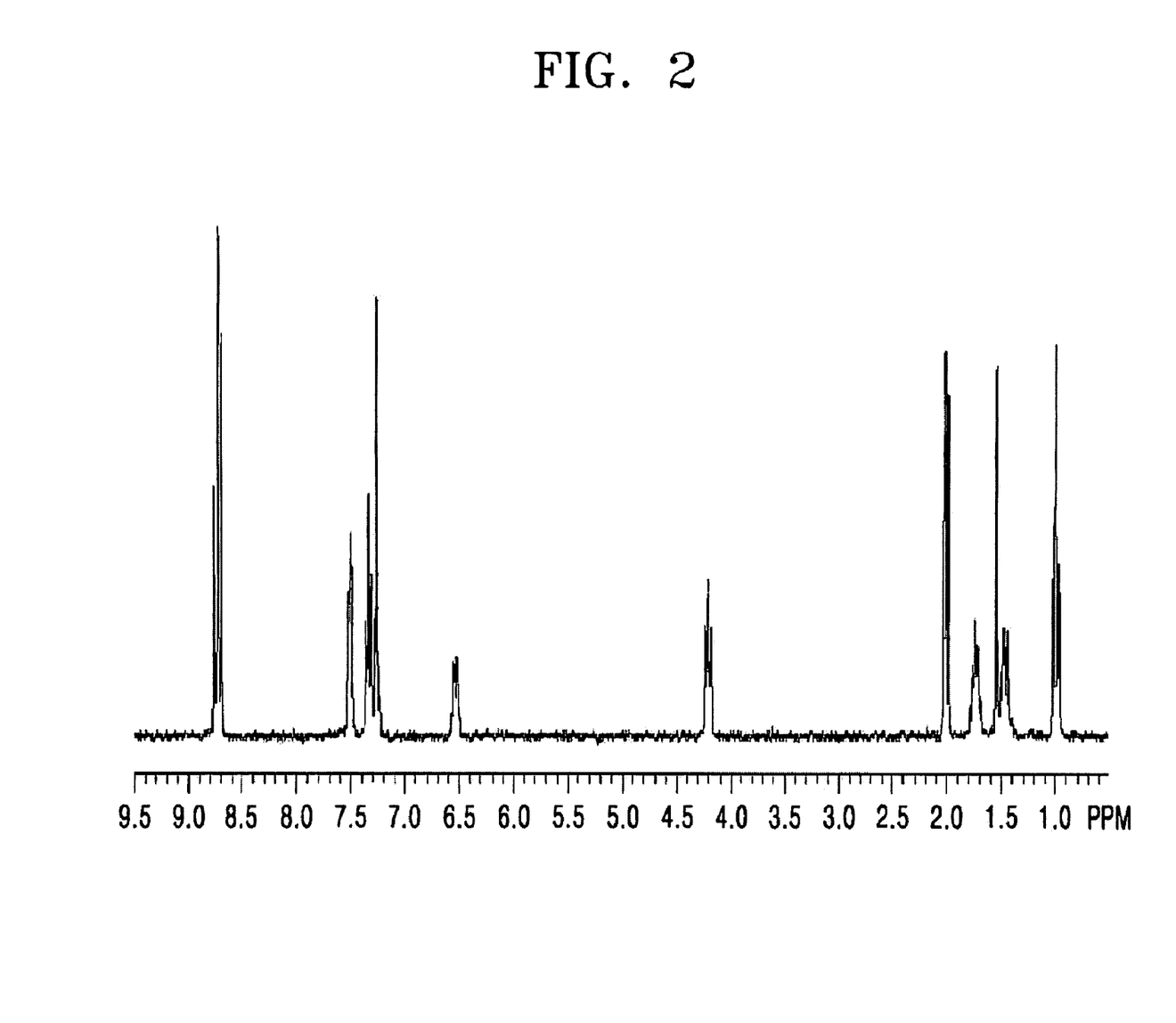
FIG. 2 is a $^1$H-NMR spectrum of naphthalenetetracarboxylic acid diimide derivative according to Preparation Example 1 of the present invention (Compound (4))

A 250 ml three neck flask equipped with a reflux condenser was purged with nitrogen, and then 16.09 g (0.06 mol) of 1,4,5,8-naphthalenetetracarboxylic acid dianhydride and 100 ml of N,N-dimethylformamide (DMF) were poured thereinto and stirred at room temperature. Then, a mixture of 7.27 g (0.06 mol) of α-methylbenzylamine, 4.39 g (0.06 mol) of n-butylamine and 20 ml of DMF was slowly added dropwise and further stirred at room temperature for an hour. The temperature of the mixture was raised and then the mixture was refluxed for 3 hours and cooled to room temperature. 200 ml of distilled water was added to the reactant, and the product was precipitated and filtered. The filtered solid was dissolved in a chloroform/ethanol solvent and boiled. Undissolved solid was removed and the remaining solution was allowed to stand at room temperature to give a crystal. The crystal was filtered and dried in a vacuum to obtain 8.7 g of Compound (4) as a crystal with a white color (yield: 35%). The $^1$H-NMR (300 MHz, CDCl$_3$ solvent) of the obtained Compound (4) is shown in FIG. 2.

Preparation Example 2

Preparation of Compound (12)

The following is a description of the preparation of an asymmetric naphthalenetetracarboxylic acid diimide Compound (12).

(12)

Figure 3:
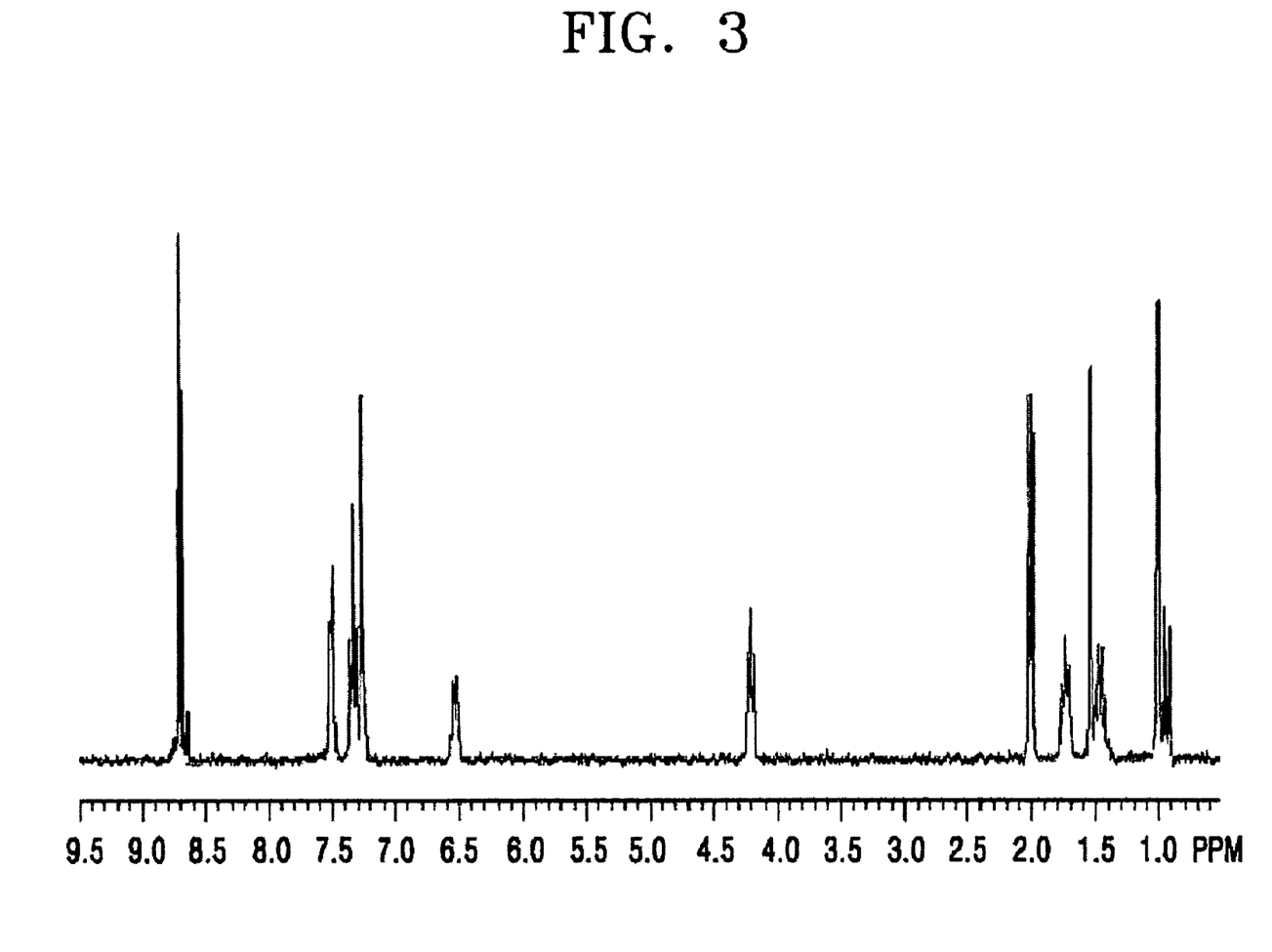
FIG. 3 is a $^1$H-NMR spectrum of naphthalenetetracarboxylic acid diimide derivative according to Preparation Example 2 of the present invention (Compound (12)).

A 250 ml three neck flask equipped with a reflux condenser was purged with nitrogen, and then 16.09 g (0.06 mol) of 1,4,5,8-naphthalenetetracarboxylic acid dianhydride and 100 ml of DMF were poured thereinto and stirred at room temperature. Then, a mixture of 8.11 g (0.06 mol) of (R)-(+)-phenylpropylamine, 4.39 g (0.06 mol) of n-butylamine and 20 ml of DMF was slowly added dropwise and further stirred at room temperature for an hour. The temperature of the mixture was raised and then the mixture was refluxed for 3 hours and cooled to room temperature. 200 ml of distilled water was added to the reactant, and the product was precipitated and filtered. The filtered solid was dissolved in a chloroform/ethanol solvent and boiled. Undissolved solid was removed and the remaining solution was allowed to stand at room temperature to give a crystal. The crystal was filtered and dried in a vacuum to obtain 8.46 g of Compound (12) as a crystal with a white color (yield: 32%). The $^1$H-NMR(300 MHz, CDCl$_3$ solvent) of the obtained Compound (12) is shown in FIG. 3.

Preparation Example 3

Preparation of Compound (30)

The following is a description of the preparation of a symmetric naphthalenetetracarboxylic acid diimide Compound (30) to be used as an ETM in Comparative Example 2.

(30)

A 250 ml three neck flask equipped with a reflux condenser was purged with nitrogen, and then 16.09 g (0.06 mol) of 1,4,5,8-naphthalenetetracarboxylic acid dianhydride and 150 ml of DMF were poured thereinto and stirred at room temperature. Then, a mixture of 14.54 g (0.12 mol) of α-methylbenzylamine, and 30 ml of DMF was slowly added dropwise and further stirred at room temperature for an hour. The temperature of the mixture was raised and then the mixture was refluxed for 3 hours and cooled to room temperature. 90 ml of methanol was added to the reactant, and the product was precipitated and filtered. The filtered solid was recrystallized in a chloroform/ethanol solvent and dried in a vacuum to obtain 23.06 g of the compound (30) as a crystal with a white color (yield: 81%).

Preparation Example 4

Preparation of Compound (40)

The following is a description of the preparation of a symmetric naphthalenetetracarboxylic acid diimide Compound (40) to be used as an ETM in Comparative Example 3.

(40)

A 250 ml three neck flask equipped with a reflux condenser was purged with nitrogen, and then 16.09 g (0.06 mol) of 1,4,5,8-naphthalenetetracarboxylic acid dianhydride and 150 ml of DMF were poured thereinto and stirred at room temperature. Then, a mixture of 8.8 g (0.12 mol) of n-butylamine and 30 ml of DMF was slowly added dropwise and further stirred at room temperature for an hour. The temperature of the mixture was raised and then the mixture was refluxed for 3 hours and cooled to room temperature. The resultant crystal was filtered and dried in a vacuum to obtain 19.3 g of the symmetric Compound (40) as a crystal with a yellow color (yield: 85%).

Preparation Example 5

Preparation of Compound (26)

The following is a description of the preparation of a dicyanofluorene-based compound Compound (26) to be used as an ETM in Comparative Example 1.

A mixture of 70 g (0.312 mole) of 9-fluorenone-4-carboxylic acid (from Sigma-Aldrich, Milwaukee, Wis.), 480 g (6.5 mole) of n-butanol (manufactured from Fisher Scientific Company Inc., Hanover Park, Ill.), 1000 ml of toluene, and 4 ml of concentrated sulfuric acid were added to a 2-liter round bottom flask equipped with a mechanical stirrer and a reflux condenser with a Dean Stark apparatus. With aggressive agitation, the solution was refluxed for 5 hours, during which time about 6 g of water was collected in the Dean Stark apparatus. After refluxing, the flask was cooled to room temperature. The solvents were evaporated and the residue was added with agitation to 4-liter of a 3% aqueous solution of sodium bicarbonate. The solid was filtered off, washed with water until the pH of the washed water was neutral, and dried under a hood overnight. The product was n-butyl 9-fluorenone-4-carboxylate ester. The yield was 70 g (80%).

A mixture of 70 g (0.25 mole) of n-butyl 9-fluorenone-4-carboxylate ester, 750 ml of absolute methanol, 37 g (0.55 mole) of malononitrile (from Sigma-Aldrich, Milwaukee, Wis.), 20 drops of piperidine (from Sigma-Aldrich, Milwaukee, Wis.) was added to a 2-liter, 3-neck round bottom flask equipped with a mechanical stirrer and a reflux condenser. The solution was refluxed for 8 hours and the flask was cooled to room temperature. The orange crude product was filtered, washed twice with 70 ml of methanol and once with 150 ml of water, and dried overnight in a hood. This orange crude product was recrystallized from a mixture of 600 ml of acetone and 300 ml of methanol using activated charcoal. The flask was placed at 0° C. for 16 hours. The crystals formed were filtered and dried in a vacuum oven at 50° C. for 6 hours to obtain 60 g of pure (4-n-butoxycarbonyl-9-fluorenylidene) malononitrile (Compound (26)).

Example 1

29.7 parts by weight of the naphthalenetetracarboxylic acid diimide Compound (4) obtained in Preparation Example 1 as ETM, 3 parts by weight of an X-type metal-free phthalocyanine Compound (20) (H2Pc) as a CGM, 14.9 parts by weight of an enaminestilbene-based Compound (22) as an HTM, 52.4 parts by weight of a binder resin Compound (24) (O-PET, available from KANEBO), 280 parts by weight of methylene chloride, and 120 parts by weight of 1,1,2-trichloroethane were sand milled for 2 hours and uniformly dispersed using ultrasonic waves.

The obtained solution was coated on an anodized aluminum drum (anodic oxide layer thickness: 5 μm) having a diameter of 3 cm by a ring coating method and dried at 110° C. for 1 hour to prepare an electrophotographic photoreceptor drum having a photosensitive layer having a thickness of about 15 to 16 μm.

(20)

(22)

(24)

(26)

Example 2

An electrophotographic photoreceptor drum was prepared in the same manner as in Example 1, except that 29.7 parts by weight of the naphthalenetetracarboxylic acid diimide Compound (12) prepared in Preparation Example 2 was used as an ETM instead of the naphthalenetetracarboxylic acid diimide Compound (4).

Comparative Example 1

An electrophotographic photoreceptor drum was prepared in the same manner as in Example 1, except that 29.7 parts by weight of the dicyanofluorene Compound (26) prepared in Preparation Example 5 was used as an ETM instead of the naphthalenetetracarboxylic acid diimide Compound (4).

Comparative Example 2

An electrophotographic photoreceptor drum was prepared in the same manner as in Example 1, except that 29.7 parts by weight of the symmetric naphthalenetetracarboxylic acid diimide Compound (30) prepared in Preparation Example 3 was used as an ETM instead of the naphthalenetetracarboxylic acid diimide Compound (4).

Comparative Example 3

An electrophotographic photoreceptor drum was prepared in the same manner as in Example 1, except that 29.7 parts by weight of the symmetric naphthalenetetracarboxylic acid diimide Compound (40) prepared in Preparation Example 4 was used as an ETM instead of the naphthalenetetracarboxylic acid diimide Compound (4).

Solubility Test 1 g of a compound to be tested was poured into a test tube with stirring at room temperature and solvents listed in Table 1 were slowly added drop by drop. The amounts of the solvents required to completely dissolve 1 g of the tested compound were measured. Table 1 demonstrates solubility test results.

TABLE 1

| | | Methylene chloride (g) | Tetrahydrofuran (g) |
|---|---|---|---|
| | Compounds | | |
| Preparation Example 1 | Compound (4) | 1.5 | 12 |
| Preparation Example 2 | Compound (12) | 1.3 | 7 |
| Preparation Example 3 | Compound (30) | 3.5 | 50 |
| Preparation Example 4 | Compound (40) | 17 | 74 |

Referring to Table 1, the asymmetric naphthalenetetracarboxylic acid diimide Compounds (4) and (12) according to the present invention have approximately 3 to 12 times better solubility in the organic solvents than the symmetric naphthalenetetracarboxylic acid diimide Compounds (30) and (40).

Long Period Charging Stability

Electrostatic properties of the respective electrophotographic photoreceptors prepared in the above Examples and Comparative Examples were measured using a scorotron-charging type drum photoreceptor evaluation apparatus manufactured by the Applicant of the present invention. The initial charge and exposure potentials and the charge and exposure potentials after 6,000 cycles were measured. The measured results are shown in Table 2. The drum photoreceptor evaluation apparatus has a drum diameter of 30 mm and a drum revolution speed of 5 ips (inch/second). The conditions of evaluation were as follows. A grid voltage (Vg)=1.0 kV, a wire current (Iw)=300 uA, and laser supply unit (LSU) electrical power=0.9 mW.

TABLE 2

| | HTM | ETM | Surface crystals | $Vd_{initial}$ (V) | $Vd_{6000}$ (V) | $\Delta Vd$ (V) | $Vo_{initial}$ (V) | $Vo_{6000}$ (V) | $\Delta Vo$ (V) |
|---|---|---|---|---|---|---|---|---|---|
| Example 1 | ○ | Compound (4) | None | 74 | 76 | 2 | 990 | 985 | 5 |
| Example 2 | ○ | Compound (12) | None | 72 | 74 | 2 | 995 | 985 | 10 |
| Comparative Example 1 | ○ | Compound (26) | None | 73 | 79 | 6 | 680 | 450 | 230 |

TABLE 2-continued

| | HTM | ETM | Surface crystals | $Vd_{initial}$ (V) | $Vd_{6000}$ (V) | Δ Vd (V) | $Vo_{initial}$ (V) | $Vo_{6000}$ (V) | Δ Vo (V) |
|---|---|---|---|---|---|---|---|---|---|
| Comparative Example 2 | ○ | Compound (30) | None | 78 | 82 | 4 | 980 | 950 | 30 |
| Comparative Example 3 | ○ | Compound (40) | Generated | 101 | 104 | 3 | 940 | 830 | 110 |

In Table 2, $V_{o\ initial}$ denotes an initial charge potential, $V_{d\ initial}$ denotes an initial exposure potential, $V_{o\ 6000}$ denotes a charge potential after 6000 cycles, and $V_{d\ 6000}$ denotes an exposure potential after 6000 cycles. $\Delta V_d$ refers to an increase in the exposure potential after 6000 cycles, i.e., $\Delta V_d = V_{d\ 6000} - V_{d\ initial}$.

$\Delta V_o$ refers to a decrease in the charge potential after 6000 cycles, i.e., $\Delta V_o = V_{o\ initial} - V_{o\ 6000}$.

Δ Vo and Δ Vd indicate changes in the surface potentials of the electrophotographic photoreceptor after several thousand cycles. When the photoreceptor having high Δ Vo and Δ Vd values is used for image forming, image qualities deteriorate with repetition of cycles.

Referring to Table 2, the photoreceptor drum prepared in Example 1 using the asymmetric naphthalenetetracarboxylic acid diimide Compound (4) as an ETM according to the present invention showed only a decrease of 5 V in charge potential after 6000 cycles (ΔVo=5 V), demonstrating that the photoreceptor drum had good stability in charge potential even after 6000 cycles. The photoreceptor drum prepared in Example 2 using the asymmetric naphthalenetetracarboxylic acid diimide Compound (12) as an ETM according to the present invention also showed only a decrease of 10 V in charge potential after 6000 cycles (Δ Vo=10 V), demonstrating that the photoreceptor drum had also good stability in charge potential even after 6000 cycles.

The photoreceptor prepared in Comparative Example 1 using the dicyanofluorenone Compound (26) as an ETM showed a charge potential lower than that of the photoreceptor prepared in Example 1 and had much poorer stability in charge potential than the photoreceptor of Example 1.

The photoreceptor drum prepared in Comparative Example 2 using as an ETM the symmetric naphthalenetetracarboxylic acid diimide Compound (30), which had poor solubility compared to the asymmetric naphthalenetetracarboxylic acid diimide Compound (4), had a lower charge potential than the photoreceptor prepared in Example 1 using the asymmetric naphthalenetetracarboxylic acid diimide Compound (4). In addition, the photoreceptor drum prepared in Comparative Example 2 exhibited reduced charge potential stability (Δ Vo=30 V).

The photoreceptor drum prepared in Comparative Example 3 using symmetric naphthalenetetracarboxylic acid diimide Compound (40) ETM, which has very poor solubility in organic solvents, underwent crystallization when used as an ETM on a surface of the drum after coating. In addition, the photoreceptor drum prepared in Comparative Example 3 showed a lower charge potential than the photoreceptor drum prepared in Example 1. Further, the photoreceptor drum prepared in Comparative Example 3 exhibited a very poor charge potential stability (Δ Vo=110 V).

With regard to a change in exposure potential (Δ Vd), the data confirms that the electrophotographic photoreceptor drums prepared in Examples 1 through 3 using asymmetric naphthalenetetracarboxylic acid diimide compounds as an ETM showed slight increases compared to those prepared in Comparative Examples 1 through 3. This confirms that the asymmetric naphthalenetetracarboxylic acid diimide compound according to the present invention provides effective electron transporting ability.

Therefore, the charge potential even after several thousand cycles may not decrease significantly in the electrophotographic photoreceptor using the asymmetric naphthalenetetracarboxylic acid diimide compound according to the present invention as an ETM. Therefore, the lifetime of the electrophotographic photoreceptor can be extended. Also, the image quality can be maintained after a use for an extended time.

As described above, the asymmetric naphthalenetetracarboxylic acid diimide compound according to the present invention has increased solubility in organic solvents and improved compatibility with binder resins. Thus, an electrophotographic photoreceptor containing the asymmetric naphthalenetetracarboxylic acid diimide compound according to the present invention can maintain a constant surface potential after being repeatedly used for an extended time. The electrophotographic photoreceptor according to the present invention provides a high image quality for an extended time.

Although a few preferred embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An electrophotographic photoreceptor comprising:
an electrically conductive substrate;
a photosensitive layer formed on the electrically conductive substrate,
wherein the photosensitive layer comprises an asymmetric naphthalenetetracarboxylic acid diimide derivative represented by Formula (1):

(1)

wherein $R_1$ and $R_2$ are independently selected from the group consisting of a substituted or unsubstituted $C_1$-$C_{20}$ alkyl group, a substituted or unsubstituted $C_1$-$C_{20}$ alkoxy group, and a hydrogen atom; $R_3$ is a linear or branched $C_1$-$C_{20}$ alkyl group and $R_4$ is an unsubstituted $C_1$-$C_{20}$ alkyl group; and Ar is a substituted or unsubstituted $C_6$-$C_{30}$ aryl group.

2. The electrophotographic photoreceptor of claim 1, wherein an intermediate layer is further provided between the electrically conductive substrate and the photosensitive layer.

3. The electrophotographic receptor of claim 1, wherein the alkyl of $R_3$ is substituted with a substituent selected from the group consisting of a halogen atom, an alkyl group, an aryl group, a nitro group, and a sulfonic acid group.

4. The electrophotographic receptor of claim 1, wherein the alkyl group of $R_3$ is selected from the group consisting of methyl, ethyl, n-propyl, isopropyl, n-butyl, isobutyl, sec-butyl, tert-butyl, pentyl, hexyl, 1,2-dimethyl-propyl and 2-ethylhexyl.

5. An electrophotographic imaging apparatus comprising an electrophotographic photoreceptor, wherein the electrophotographic photoreceptor comprises:
   an electrically conductive substrate;
   a photosensitive layer formed on the electrically conductive substrate,
   wherein the photosensitive layer comprises an asymmetric naphthalenetetracarboxylic acid diimide derivative represented by Formula (1):

(1)

wherein $R_1$ and $R_2$ are independently selected from the group consisting of a substituted or unsubstituted $C_1$-$C_{20}$ alkyl group, a substituted or unsubstituted $C_1$-$C_{20}$ alkoxy group, and a hydrogen atom; $R_3$ is a linear or branched $C_1$-$C_{10}$ to alkyl and $R_4$ is an unsubstituted $C_1$-$C_{20}$ alkyl group; and Ar is a substituted or unsubstituted $C_6$-$C_{30}$ aryl group.

6. The electrophotographic photoreceptor of claim 5, an intermediate layer is further provided between the electrically conductive substrate and the photosensitive layer.

7. The electrophotographic imaging apparatus of claim 5, wherein the alkyl of $R_3$ is substituted with a substituent selected from the group consisting of a halogen atom, an alkyl group, an aryl group, a nitro group, and a sulfonic acid group.

8. The electrophotographic imaging apparatus of claim 5, wherein the alkyl group of $R_3$ is selected from the group consisting of methyl, ethyl, n-propyl, isopropyl, n-butyl, isobutyl, sec-butyl, tert-butyl, pentyl, hexyl, 1,2-dimethyl-propyl and 2-ethylhexyl.

9. An electrophotographic cartridge comprising:
   an electrophotographic photoreceptor comprising an electrically conductive substrate, and a photosensitive layer formed on the electrically conductive substrate, wherein the photosensitive layer comprises an asymmetric naphthalenetetracarboxylic acid diimide derivative represented by Formula (1):

(1)

wherein $R_1$ and $R_2$ are independently selected from the group consisting of a substituted or unsubstituted $C_1$-$C_{20}$ alkyl group, a substituted or unsubstituted $C_1$-$C_{20}$ alkoxy group, and a hydrogen atom; $R_3$ is a linear or branched $C_1$-$C_{20}$ alkyl and $R_4$ is an unsubstituted $C_1$-$C_{20}$ alkyl group; and Ar is a substituted or unsubstituted $C_6$-$C_{30}$ aryl group; and
   at least one selected from the group consisting of a charging device that charges the electrophotographic photoreceptor, a developing device that develops an electrostatic latent image formed on the electrophotographic photoreceptor, and a cleaning device that cleans a surface of the electrophotographic photoreceptor, the electrophotographic cartridge being attachable to or detachable from an imaging apparatus.

10. The electrophotographic cartridge of claim 9, wherein an intermediate layer is further provided between the electrically conductive substrate and the photosensitive layer.

11. The electrophotographic cartridge of claim 9, wherein the alkyl of $R_3$ is substituted with a substituent selected from the group consisting of a halogen atom, an alkyl group, an aryl group, a nitro group, and a sulfonic acid group.

12. The electrophotographic cartridge of claim 9, wherein the alkyl group of $R_3$ is selected from the group consisting of methyl, ethyl, n-propyl, isopropyl, n-butyl, isobutyl, sec-butyl, tert-butyl, pentyl, hexyl, 1,2-dimethyl-propyl and 2-ethylhexyl.

13. An electrophotographic imaging apparatus comprising:
   a photoreceptor unit comprising an electrically conductive substrate, and a photosensitive layer formed on the electrically conductive substrate, wherein the photosensitive layer comprises an asymmetric naphthalenetetracarboxylic acid diimide derivative represented by Formula (1):

(1)

wherein $R_1$ and $R_2$ are independently selected from the group consisting of a substituted or unsubstituted $C_1$-$C_{20}$ alkyl group, a substituted or unsubstituted $C_1$-$C_{20}$ alkoxy group, and a hydrogen atom; $R_3$ is a linear or branched $C_1$-$C_{20}$ alkyl group and $R_4$ is an unsubstituted $C_1$-$C_{20}$ alkyl group; and Ar is a substituted or unsubstituted $C_6$-$C_{30}$ aryl group;
   a charging device that charges the photoreceptor unit;
   an imagewise light irradiating device that irradiates the charged photoreceptor unit with imagewise light to form an electrostatic latent image on the photoreceptor unit;
   a developing unit that develops the electrostatic latent image with a toner to form a toner image on the photoreceptor unit; and
   a transfer unit that transfers the toner image onto a receiving material.

14. electrophotographic imaging apparatus of claim 13, an intermediate layer is further provided between the electrically conductive substrate and the photosensitive layer.

15. The electrophotographic imaging apparatus of claim 13, wherein the alkyl of $R_3$ is substituted with a substituent selected from the group consisting of a halogen atom, an alkyl group, an aryl group, a nitro group, and a sulfonic acid group.

16. The electrophotographic imaging apparatus of claim 13, wherein the alkyl group of $R_3$ is selected from the group consisting of methyl, ethyl, n-propyl, isopropyl, n-butyl, isobutyl, sec-butyl, tert-butyl, pentyl, hexyl, 1,2-dimethylpropyl and 2-ethylhexyl.

17. An electrophotographic photoreceptor comprising a naphthalenetetracarboxylic acid diimide derivative selected from the group consisting of

(1)

(2)

(3)

(4)

(5)

(6)

-continued

(7)

(8)

(9)

(10)

(11)

(12)

-continued (13)

(14)

(15)

(16)

* * * * *